(12) United States Patent
Winslow et al.

(10) Patent No.: US 8,795,279 B2
(45) Date of Patent: Aug. 5, 2014

(54) PERIPHERAL PEG DRILL COMPONENT

(75) Inventors: Nathan A. Winslow, Warsaw, IN (US);
Ben Joseph, Fort Wayne, IN (US);
Daniel Duane Fritzinger, Warsaw, IN (US); Clinton Kehres, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 177 days.

(21) Appl. No.: 13/472,738

(22) Filed: May 16, 2012

(65) Prior Publication Data

US 2013/0309030 A1 Nov. 21, 2013

(51) Int. Cl.
*A61B 17/00* (2006.01)
(52) U.S. Cl.
USPC ............................................. 606/80; 606/81
(58) Field of Classification Search
USPC ........ 606/79–81, 180; 408/25, 42, 53; 407/43
See application file for complete search history.

(56) References Cited

U.S. PATENT DOCUMENTS

| 2,835,035 | A | 5/1958 | Wolfdietrich |
| 4,197,645 | A | 4/1980 | Scheicher |
| 6,190,383 | B1* | 2/2001 | Schmaltz et al. ............... 606/41 |
| 7,059,812 | B2* | 6/2006 | McFarlane ....................... 408/53 |

OTHER PUBLICATIONS

International Search Report & Written Opinion of the International Searching Authority from the EPO for Int. PCT Application No. PCT/US2013/039020, dated Aug. 12, 2013, 11 pages.

* cited by examiner

*Primary Examiner* — Andrew Yang
(74) *Attorney, Agent, or Firm* — Taft Stettinius & Hollister LLP; Ryan O. White

(57) ABSTRACT

A peripheral peg drill component comprising a housing having a first side and a second side opposite the first side, at least two drill bits extending from the second side of the housing, a defined opening on the second side of the housing, the defined opening being configured to receive an alignment pin extending from a bony surface, and a driving mechanism within the housing, the driving mechanism being configured to rotate the at least two drill bits and cause them to simultaneously penetrate the bony surface.

11 Claims, 12 Drawing Sheets

PERIPHERAL PEG DRILL COMPONENT

TECHNICAL FIELD

The present invention generally relates to a surgical drill component, and more particularly, a peripheral peg drill component that can be used as part of a glenoid replacement surgical procedure.

BACKGROUND OF THE INVENTION

The statements in this section merely provide background information related to the present disclosure and should not be construed as constituting prior art.

A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of a shoulder joint prosthesis becomes necessary, the natural head portion of the humerus can be resected and a cavity created in the intramedullary canal of the host humerus for accepting a humeral component. Moreover, the glenoid cavity positioned at the lateral edge of the scapula may also be resurfaced and shaped to accept the glenoid component. The humeral component includes a head portion used to replace the natural head of the humerus, while the glenoid component generally includes an articulating surface which is engaged by the head portion of the humeral component.

It is generally known in the art to provide a shoulder joint prosthesis having a glenoid component, as discussed above. Current glenoid replacement surgical techniques, however, suffer from some disadvantages, particularly as they require the surgeon to perform numerous bone preparation steps before the glenoid component can be surgically implanted. More particularly, since glenoid components are subject to various types of loading by the head portion of the humeral component, the glenoid component must offer a stable and secure articulating surface. To achieve this, some glenoid components provide peripheral pegs which are inserted and cemented into holes bored into the glenoid cavity. Some of the pegged glenoid components utilize up to five peripheral pegs in order to stabilize and secure the glenoid component to the scapula. Current glenoid replacement procedures require pre-drilled holes to be formed in the bone for each peripheral peg of the glenoid component. To achieve this, typically a guide is placed on the glenoid that provides a path for each peripheral peg hole to be drilled. After each hole is drilled, an anti-rotation peg is inserted into that respective hole of the guide to ensure the next drilled hole is properly aligned. By requiring multiple holes to be separately drilled into the bone, not only is the process time-consuming, but it also increases the possibility that a drilling misalignment will occur during the bone preparation process.

What is needed then is a device that can be incorporated into a glenoid replacement surgical technique without suffering from the above-mentioned disadvantages. The present invention is intended to improve upon and resolve some of these known deficiencies of the art.

SUMMARY OF THE INVENTION

In accordance with one aspect of the present invention, a peripheral peg drill component is provided. The drill component comprises a housing having a first side and a second side opposite the first side, at least two drill bits extending from the second side of the housing, a defined opening on the second side of the housing, the defined opening being configured to receive an alignment pin extending from a bony surface, and a driving mechanism within the housing, the driving mechanism being configured to rotate the at least two drill bits and cause them to simultaneously penetrate the bony surface.

According to another aspect of the present invention, a peripheral peg drill component comprises a housing having a first side and a second side opposite the first side, at least two drill bits extending from the second side of the housing, a movable boss associated with the second side of the housing, the movable boss defining an opening that is configured to receive an alignment pin extending from a bony surface, a driving mechanism within the housing, and a drive shaft actuatable by a drill and configured to cause the driving mechanism to rotate the at least two drill bits so that they simultaneously penetrate the bony surface.

In accordance with still another aspect of the present invention, a method for simultaneously drilling at least two peripheral peg holes in a bony surface is provided. According to this illustrative embodiment, the method comprises the steps of: providing a peripheral peg drill component including a housing with a first side, a second side opposite the first side and at least two drill bits extending from the second side of the housing; releasably coupling the first side of the peripheral peg drill component to a drilling device; advancing the peripheral peg drill component over an alignment pin extending from a bony surface until each of the at least two drill bits engage the bony surface; actuating a driving mechanism of the peripheral peg drill component with the drilling device to cause the at least two drill bits to rotate; and simultaneously penetrating the bony surface with the at least two drill bits as they rotate.

Still other objects and benefits of the invention will become apparent from the following written description along with the accompanying figures.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Figure 1:
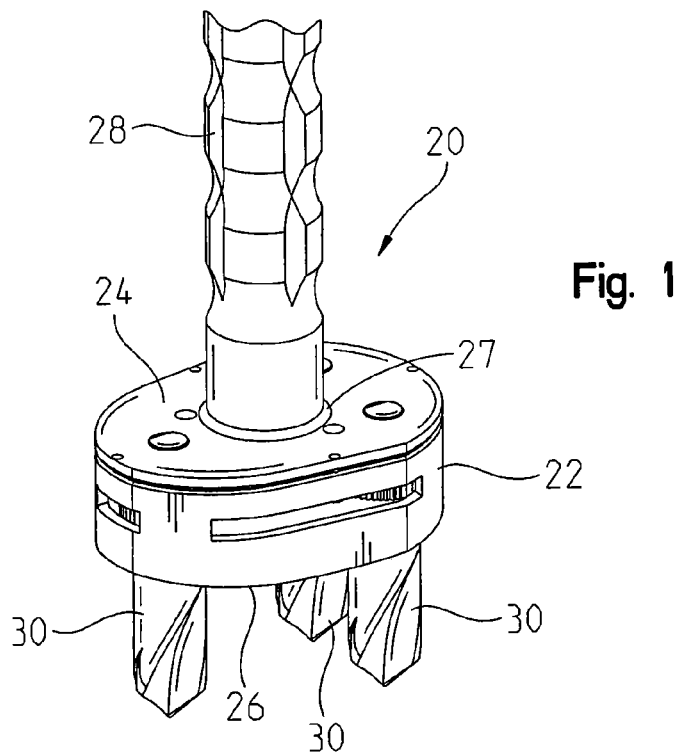
FIG. 1 represents a perspective view of a peripheral peg drill component according the present teachings.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described. Moreover, the techniques employed or contemplated herein are standard methodologies well known to one of ordinary skill in the art and the materials, methods and examples are illustrative only and not intended to be limiting.

Figure 2:
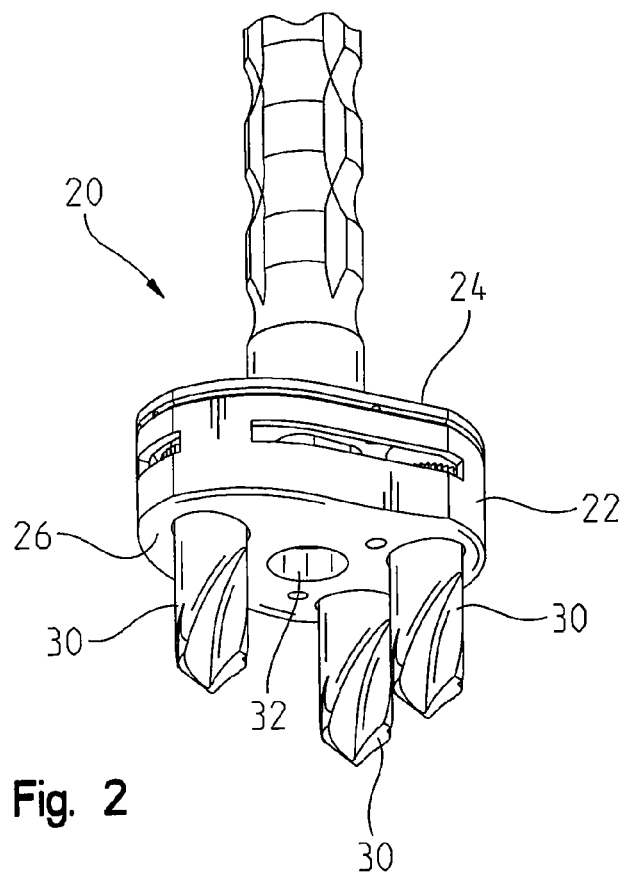
FIG. 2 represents a perspective bottom view of the peripheral peg drill component of FIG. 1.

Referring generally to FIGS. 1 and 2, perspective views of a peripheral peg drill component 20 according to the teachings of the present application are shown. The peripheral peg drill component 20 is defined by a housing 22 having a first side 24 and a second side 26. The first side 24 of the housing 22 includes a defined opening 27 that is configured to receive the drive shaft 28 of a drill, while the second side 26 has one or more drill bits 30 extending therefrom and configured to create peripheral peg holes in a glenoid cavity upon actuation of the drilling device. In terms of the structural means by which the drive shaft 28 is connected to the housing 22 of the peripheral peg drill component 20, it should be understood and appreciated herein that any known connection means may be utilized without straying from the teachings and scope of the present application. For instance, in accordance with one specific illustrative embodiment, a conventional Hudson connection can be utilized. In accordance with yet other illustrative embodiments, the drive shaft can be releasably secured to the peripheral peg drill component 20 by a connection means including, but not limited to, a square-drive quick-connection, a conventional drill chuck mechanism, a set screw, a tool clamp, a rivet, a snap ring, a press-fit, or the like. As such, the present teachings are not intended to be limited herein.

As is particularly shown in FIG. 2, the second side 26 of the peripheral peg drill component 20 includes a substantially centralized and defined opening 32 that is configured to receive a guide or alignment pin 34 (see FIG. 5) that has been inserted into the glenoid cavity 36 as part of the glenoid preparation process. As will be explained in more detail below, in accordance with certain alternative aspects of the present invention (see FIG. 13), it should be understood and appreciated that instead of having a defined opening 32, the housing 22 can alternatively have a movable centralized boss 33 that is configured to move from a first position within the housing 22 to a second position outside of the housing 22. In accordance with this embodiment, the centralized boss 33 can have a geometry that substantially matches the geometry of the pre-reamed glenoid cavity 36 to thereby ensure proper alignment and orientation of the drill component within the glenoid cavity when it is extended outside of the housing 22.

Figure 3:
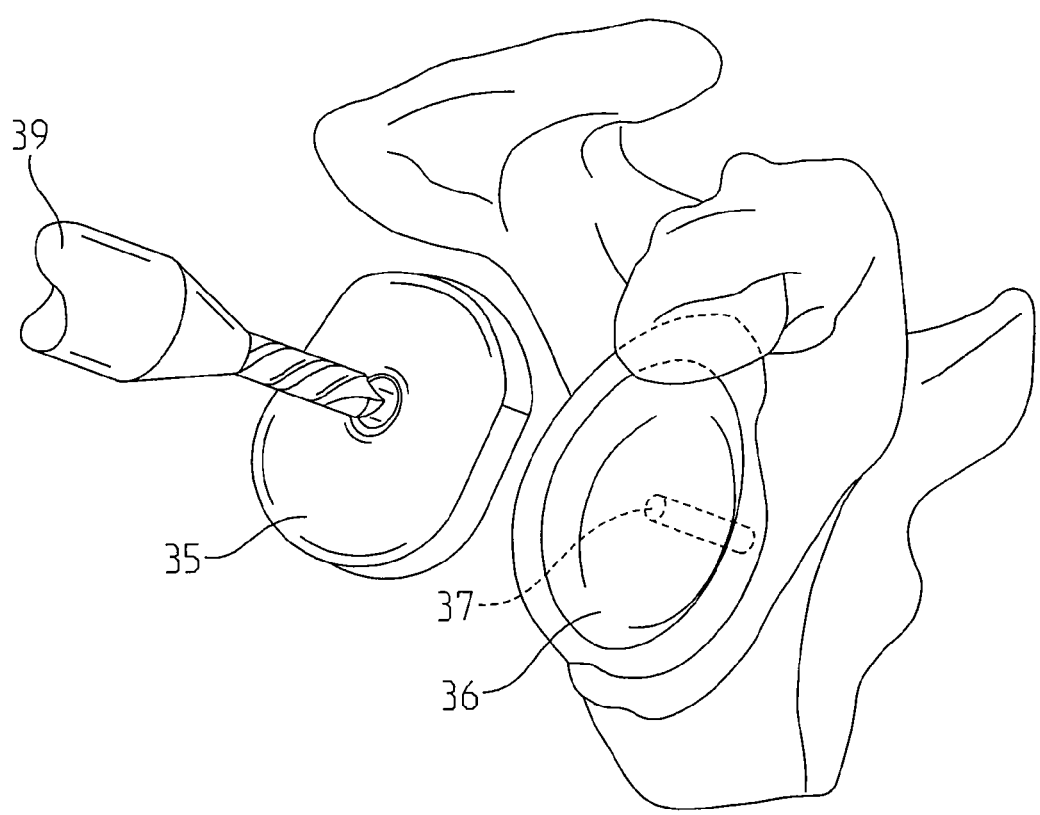
FIGS. 3-5 represent perspective views of a glenoid cavity being prepared prior to the implantation of a glenoid component according to the present teachings.
Figure 4:
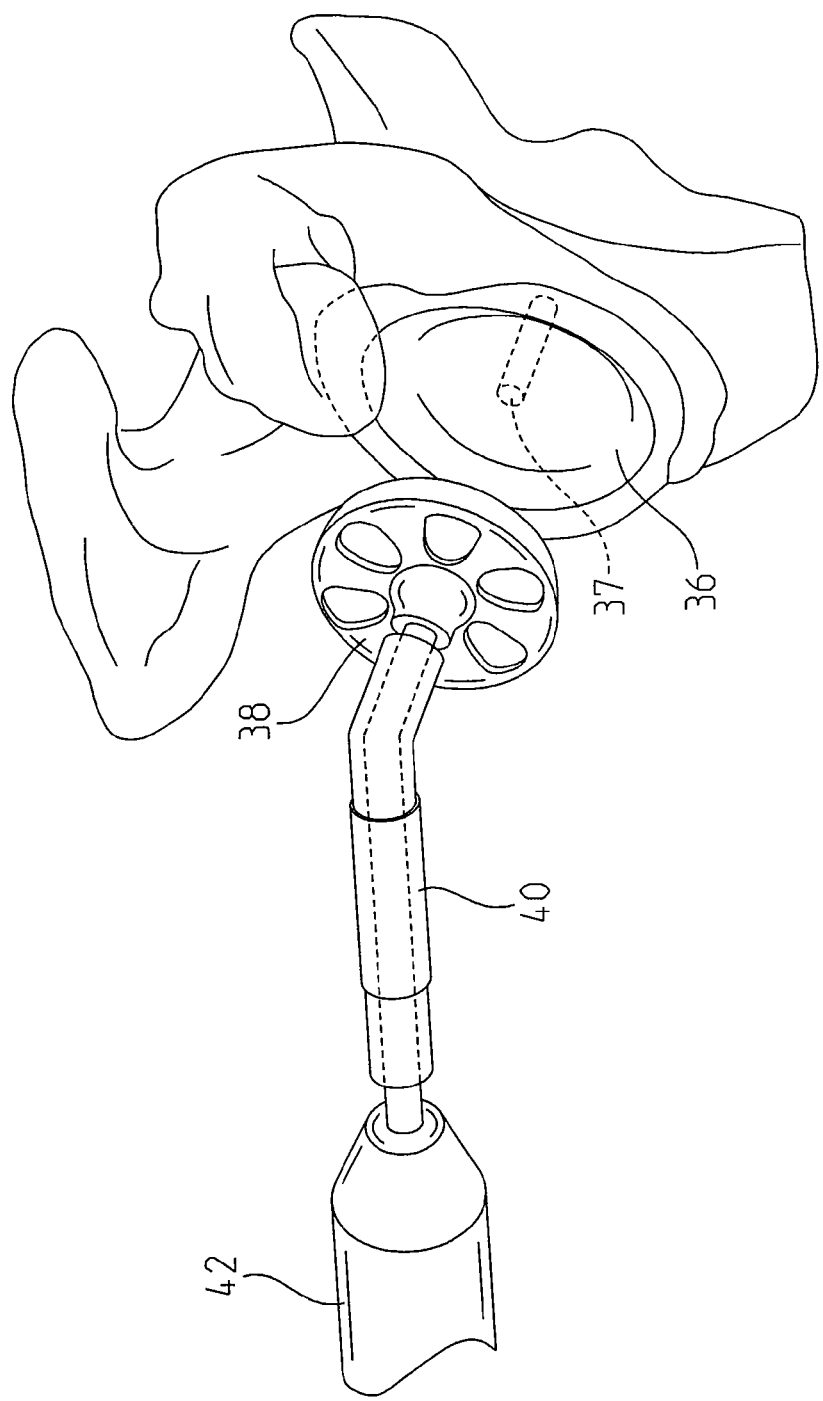
Figure 5:
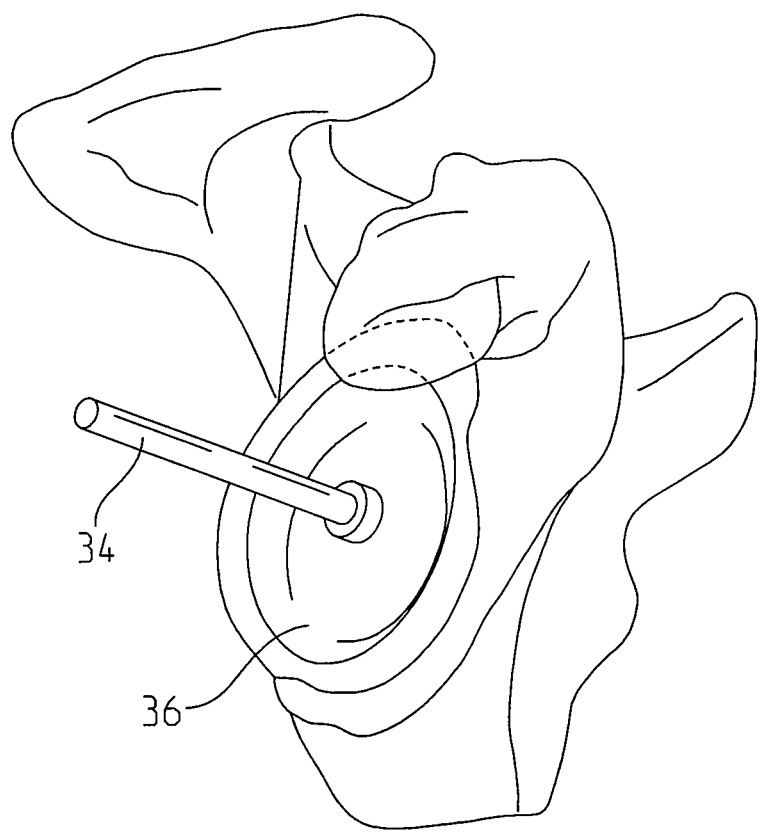

FIGS. 3-5 represent an illustration of an exemplary process for preparing a glenoid prior to implanting a glenoid component according to the teachings of the present application. As shown in FIG. 3, a drilling guide 35 can be used to create a central guide hole 37 into the surface of the glenoid cavity 36 using a drill 39. After the preparation of a central guide hole 37, as shown in FIG. 4, the glenoid cavity 36 is reamed using a glenoid surface rasp 38 and an angled reamer shaft 40 with driver 42. As those of skill in the art will understand and appreciate, the glenoid surface rasp 38 is configured to prepare a planar or curved glenoid surface to mate with the coupling side of the glenoid component to be implanted. To accomplish this, the glenoid surface rasp 38 may include a roughened spherical surface that substantially corresponds to the spherical shape of the medial surface of the glenoid component.

Once the surface of the glenoid cavity has been prepared, conventional surgical glenoid replacement processes typically require that a plurality of fixed glenoid peg accepting holes be individually drilled into the resected glenoid. To accomplish this, a drilling guide is placed on the glenoid and is used as a template to provide a path for each peripheral peg hole to be drilled. After each hole is drilled, an anti-rotation peg is inserted into that respective hole of the guide to ensure the next drilled hole is properly aligned.

Figure 6:
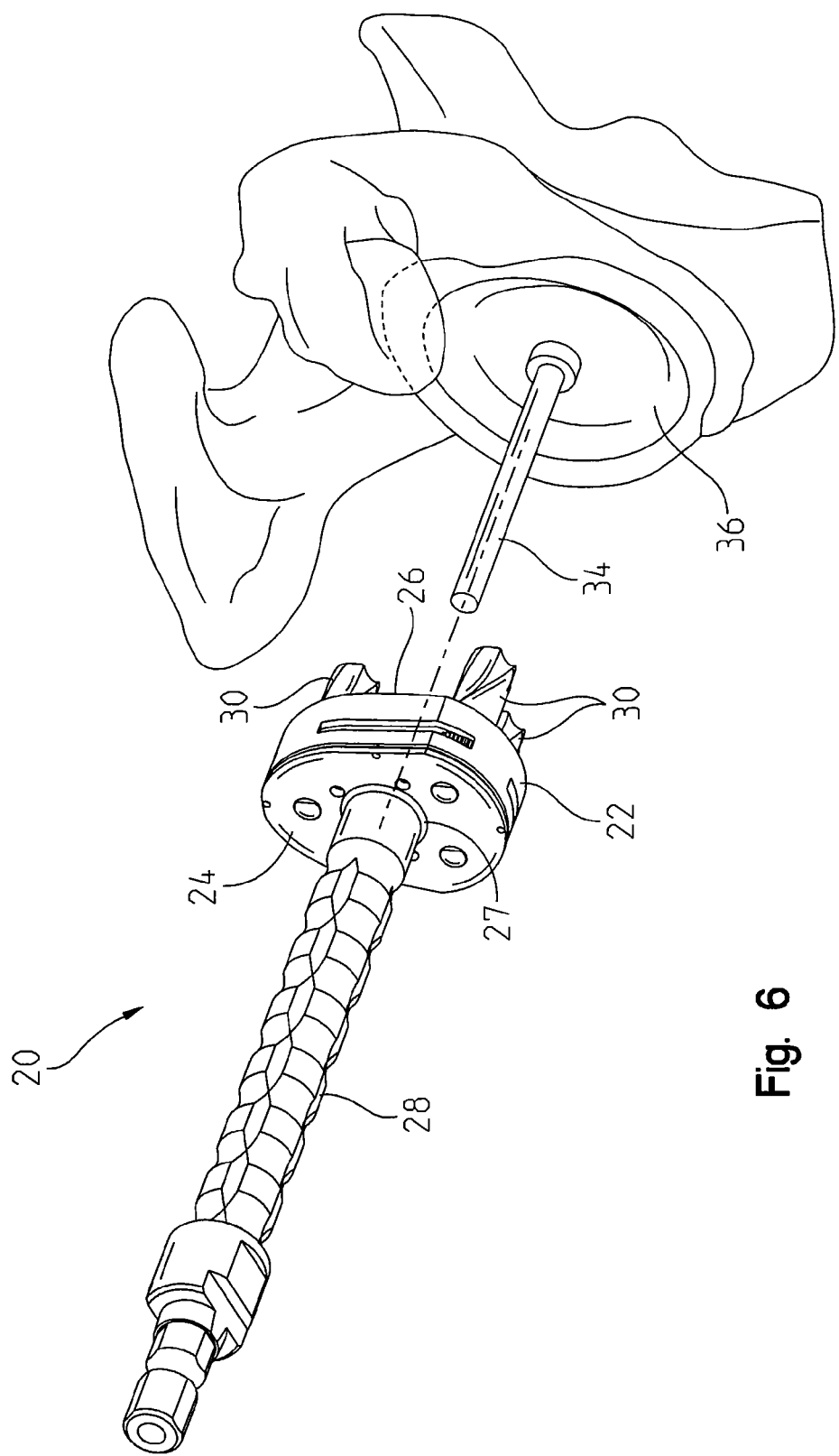
FIGS. 6-7 represent perspective views of a peripheral peg drill component in accordance with the present teachings being advanced along a guide pin prior to peripheral peg holes being drilled into a glenoid.
Figure 7:
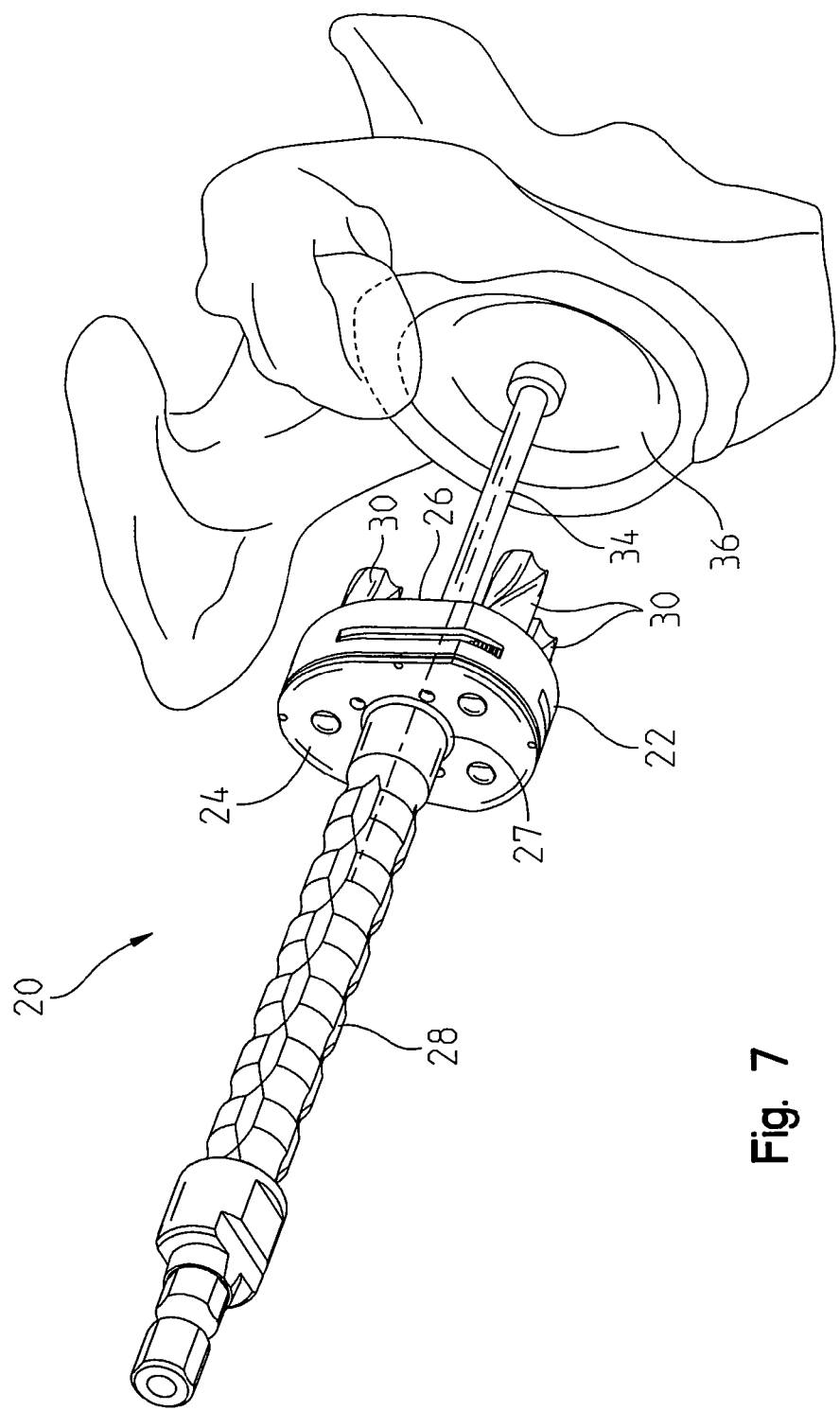
Figure 8:
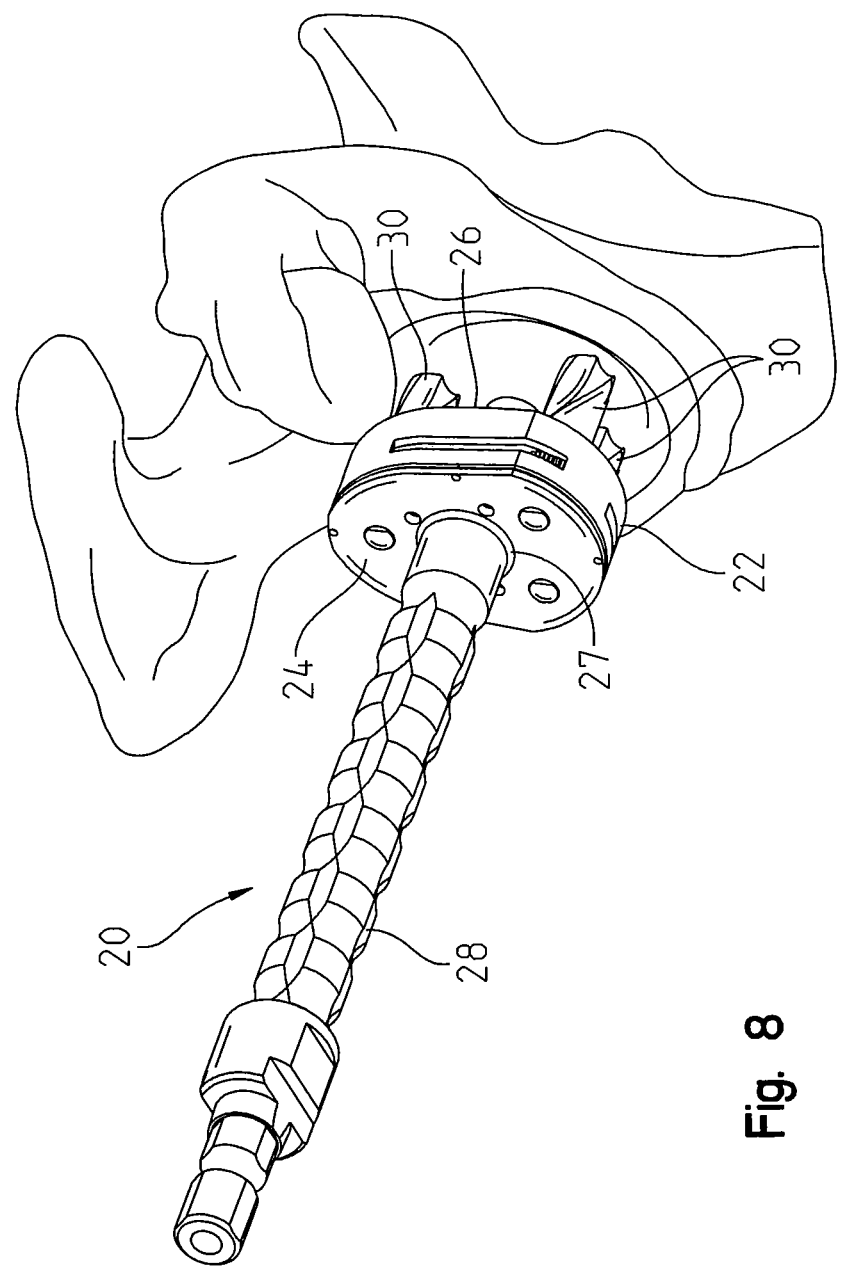
FIG. 8 represents a perspective view of a peripheral peg drill component drilling peripheral peg holes into a glenoid in accordance with the present teachings.

The present teachings, however, eliminate the need to drill each hole individually, and instead provide a means for drilling all peripheral peg holes at once. To achieve this, as shown in FIG. 5, a guide or alignment pin 34 is placed in the central guide hole 37 of the glenoid cavity 36 and is configured to penetrate the defined opening 32 positioned on of the second side 26 of the housing 22. In other words, and with reference to FIGS. 6-7, the defined opening 32 on the second side 26 of the peripheral peg drill component 20 is aligned with and advanced along the guide pin 34 until the peripheral peg drill bits 30 engage the surface of the glenoid cavity 36. After the peripheral peg drill bits 30 engage the glenoid cavity 36, the drill can be activated, thereby allowing all peripheral peg holes to be created simultaneously at once (see FIG. 8). The material from which the peripheral peg drill bits 30 are made depends on the intended application of the drill bit. For orthopedic uses, however, the drill bits 30 can be manufactured from any surgical quality metallic component including, but not limited to, stainless steel, titanium, aluminum, brass, cobalt chrome molybdenum alloys, nitinol alloys and the like. It should also be understood and appreciated herein that the size, orientation and number of drill bits 30 (and/or their respective flutes) can be adjusted as necessary, particularly depending on the intended application and use of the drill bits. In accordance with one specific embodiment, the peripheral peg drill component 20 has at least two drill bits 30 extending from the second side 26 of the housing 22, while in accordance with still other specific embodiments, at least three drill bits 30 extend from the second side 26. As such, the present teachings are not intended to be limited herein.

Figure 9:
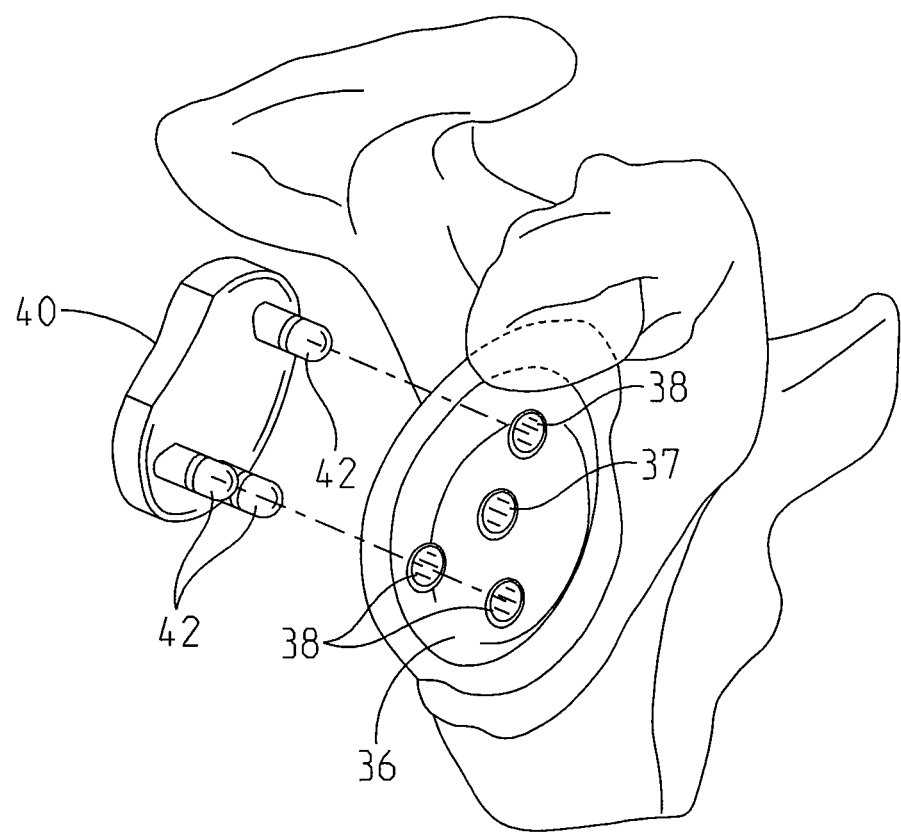
FIG. 9 represents a perspective view of a glenoid pegged component aligned for insertion into the drilled peripheral peg holes of the glenoid according to the present teachings.

As shown in FIG. 9, after the peripheral peg holes 38 are created, a glenoid component 40 can be implanted into the resected glenoid cavity 36 by aligning the peripheral pegs 42 of the glenoid component 40 with the drilled peripheral peg holes 38. It should be understood and appreciated herein that the teachings of the present application can be performed using various different geometrical peg configurations and shapes. For instance, while the present application depicts an illustrative embodiment in which the glenoid component 40 has three peripheral pegs 42, it is of course possible to perform the teachings of the present application using less or more than three peripheral pegs if desired. While not shown here, it is also envisioned that bone cement and/or various appropriate biological materials can be injected into the peripheral peg holes 38 defined within the glenoid cavity 36 before the peripheral pegs 42 of the glenoid component 40 are implanted to facilitate bonding of the component to the bone if desired. Those of skill in the art will understand how to incorporate such materials into the implantation system if necessary; therefore, a detailed discussion of the bonding process is not discussed in detail herein.

Figure 10:
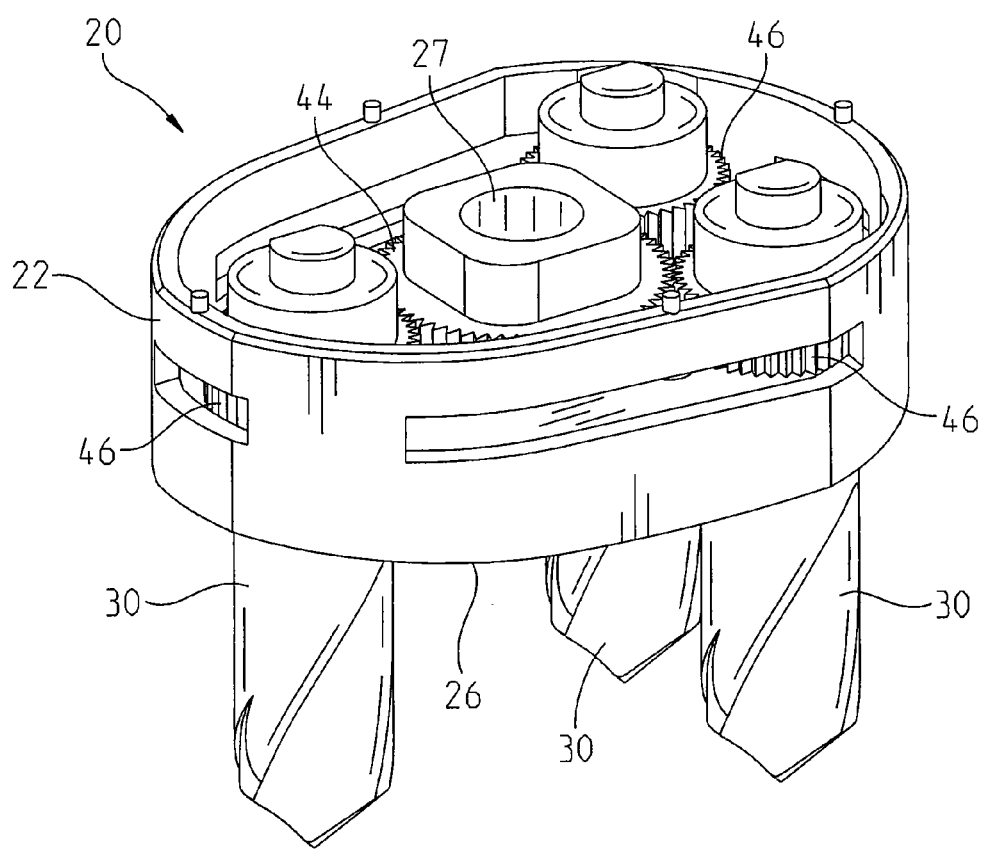
FIG. 10 represents a perspective view of a peripheral peg drill component having its top cover removed to reveal the internal driving mechanism in accordance with the present teachings.
Figure 11:
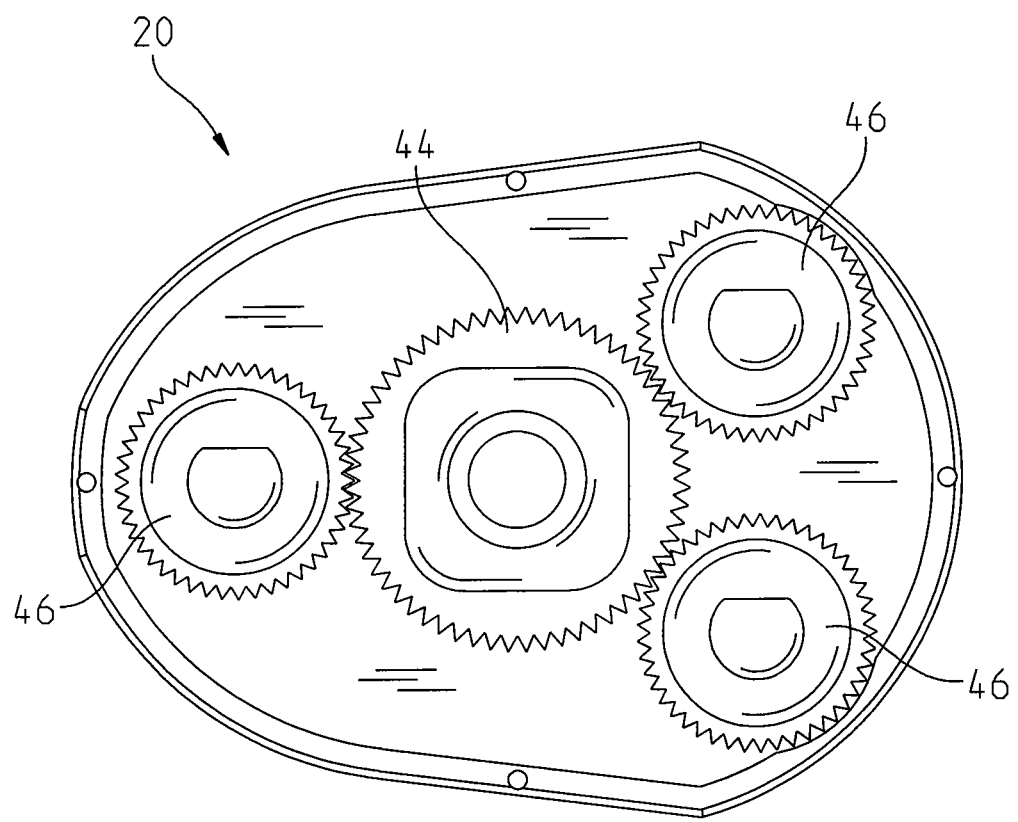
FIG. 11 represents a top view of a peripheral peg drill component having its top cover removed to reveal a spur gear system for driving the peripheral peg drill component according to the present teachings.
Figure 12:
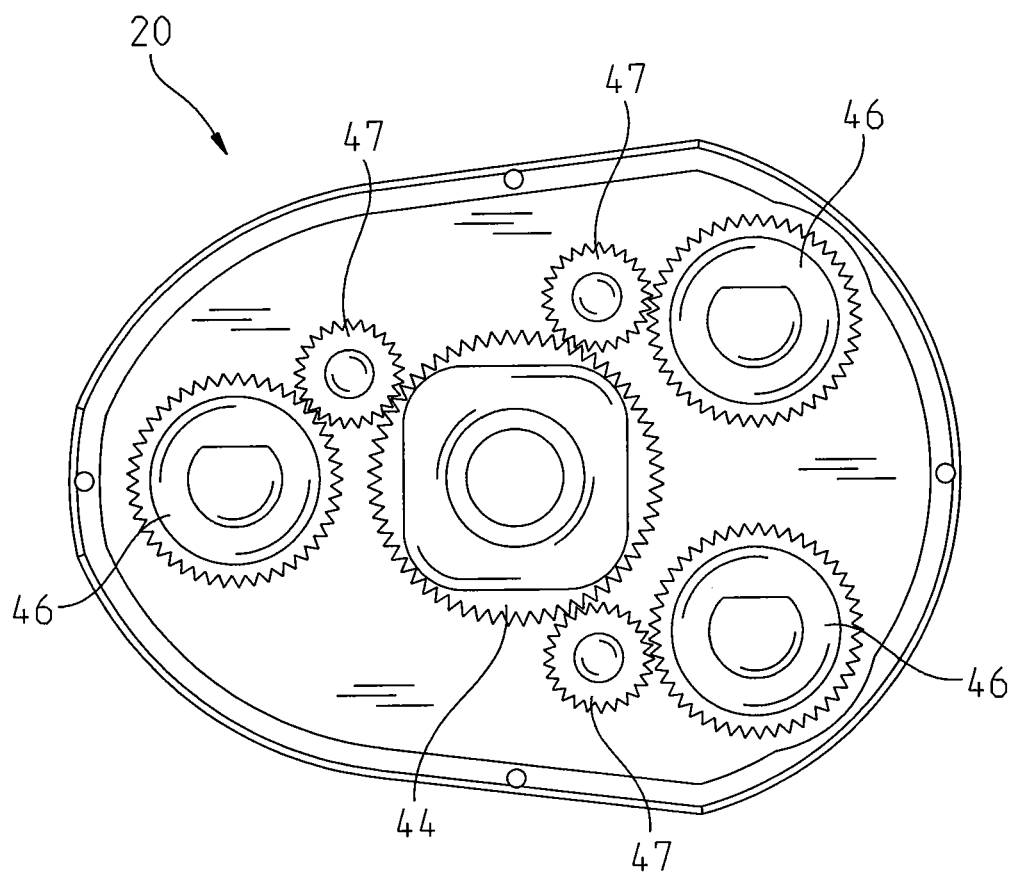
FIG. 12 represents a top view of a peripheral peg drill component having its top cover removed to reveal another spur gear system for driving the peripheral peg drill component according to the present teachings.

It should be understood and appreciated herein that various means can be used to drive the peripheral peg drill bits 30 so that the peripheral peg holes 38 are created in the glenoid cavity 36. FIGS. 10-12, for instance, depict two illustrative means for driving the drill bits 30 of the peripheral peg drill component 20 by using spur gear systems. Specifically, FIGS. 10 and 11 illustrate a standard spur gear system. Spur gear systems are generally known in the art and include various configurations of gear wheels, each having projections (teeth) that are configured to intersect or mesh with the teeth of another gear wheel, thereby transmitting force and motion alternatively from one gear to another. As is shown in this illustrative embodiment, a drive gear 44 is connected to three driven gears 46, each of which are connected to and configured to drive one of the corresponding peg drill bits 30 extending from the second side 26 of the housing 22. When a drill connected to the drive shaft 28 is activated, the drive shaft 28 will cause the drive gear 44 to rotate. Because the three driven gears 46 have teeth meshing with the teeth of the drive gear 44, the driven gears 46 will be caused to rotate in the opposite direction of the drive gear 44 as it rotates. Despite rotating in the opposite direction from the drive gear 44, each of the three driven gears 46 will still rotate in the same direction as one another, and in turn, will cause their corresponding peg drill bits 30 of which they are individually associated to rotate in the same direction in unison as well. In accordance with certain variations of this illustrative embodiment, it is also possible to have more than one gear stacked on top of one another, such that each gear has a different diameter for mating up with a gear on each peripheral drill bit 30. Such an arrangement would allow for non-symmetrical drill locations. Moreover, in accordance with certain aspects of the present invention, the internal drive mechanism can be designed in such a manner as to create counter-clockwise turning of the drill bits to accommodate left hand cutting procedures. Accordingly, the present teachings are not intended to be limited herein.

As is shown in FIG. 12, in accordance with other illustrative embodiments of the present invention, the spur gear system used for driving the drill bits 30 of the peripheral peg drill component 20 can also include additional intermediary idler gears 47 positioned between each of the driven gears 46 and the drive gear 44. As those of skill in the art will understand and appreciate, the addition of idler gears 47 can be used to keep the directional rotation of the driven gears 46 and the drive gear 44 to stay the same as the drive shaft.

As is briefly mentioned above and with illustrative reference to FIG. 13, in accordance with certain aspects of the present invention, the second side 26 of the peripheral peg drill component can be configured to include a movable centralized boss 33 that can transition between a first position within the housing 22 to a second position outside of the housing 22. The centralized boss 33 can also have a geometry that substantially matches the geometry of the pre-reamed glenoid cavity 36 such that a conformed surface mating occurs when the centralized boss 33 is extended into the reamed glenoid cavity 36. In accordance with certain embodiments, and to help control the orientation of the peripheral peg drill bits 30 relative to the pre-reamed glenoid and the central boss geometry, the centralized boss 33 and/or the peripheral drill bits 30 can be collapsible within the housing 22. In accordance with such embodiments, the collapsibility of the centralized boss 33 and/or the drill bits 30 make it easier to center the drill component 20 on the surface of the pre-reamed glenoid cavity 36 before the peripheral peg drill bits 30 engage bone.

Figure 13:
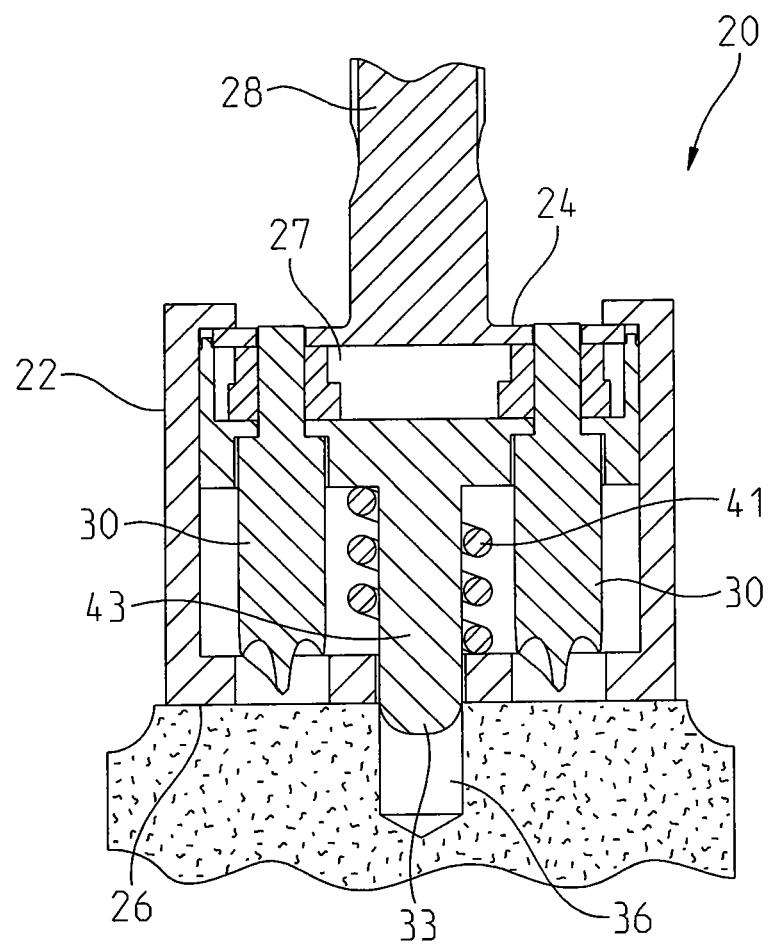
FIG. 13 represents a cross-sectional view of a collapsible peripheral peg drill component according to the present teachings.

It should be understood and appreciated herein that there are numerous ways to accomplish the collapsibility of the centralized boss 33 and/or the drill bits 30 within the housing 22. For instance, as shown in FIG. 13, a compression spring 41 can be disposed on a shaft 43 of the centralized boss 33 such that when the centralized boss 33 is advanced into glenoid cavity 36 as the second side 26 of the drill component contacts bone, the spring 41 compresses, and in turn causes the peripheral peg drill bits 30 to collectively extend out from the housing 22 as a single unit. In accordance with yet other embodiments, however, it is envisioned that each peripheral peg drill bit 30 can have its own compression spring, whereby each drill bit 30 is able to individually extend out of the housing in response to contact with the bone surface. Such an arrangement would be particularly useful for situations in which the surface of glenoid cavity 36 is uneven and requires the drill bits 30 to retract at different levels in order to achieve a proper surface alignment of the drill component within the glenoid cavity.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

What is claimed is:

1. A peripheral peg drill component, comprising:
   a housing having a first side and a second side opposite the first side;
   at least two drill bits extending from the second side of the housing,
   a defined opening on the second side of the housing, the defined opening being configured to receive an alignment pin extending from a bony surface; and
   a driving mechanism within the housing, the driving mechanism being configured to rotate the at least two drill bits and cause them to simultaneously penetrate the bony surface, wherein the driving mechanism is a spur gear system having a drive gear, at least two driven gears and at least two idler gears, each idler gear of which is positioned between the drive gear and one of the at least two driven gears.

2. The peripheral peg drill component of claim 1, wherein the at least two driven gears are each independently associated with and configured to simultaneously rotate in the same direction as one of the at least two drill bits.

3. The peripheral peg drill component of claim 1, wherein the at least two drill bits are configured to collapse into the housing as the bony surface is engaged.

4. The peripheral peg drill component of claim 1, further comprising a drive shaft releasably coupled to the first side of the housing, the drive shaft being connectable to a drill and configured to actuate the driving mechanism in response to the drill.

5. A peripheral peg drill component, comprising:
   a housing having a first side and a second side opposite the first side;
   at least two drill bits extending from the second side of the housing,
   a movable boss associated with the second side of the housing, the movable boss defining an opening that is configured to receive an alignment pin extending from a bony surface;
   a driving mechanism within the housing; and
   a drive shaft actuatable by a drill and configured to cause the driving mechanism to rotate the at least two drill bits so that they simultaneously penetrate the bony surface.

6. The peripheral peg drill component of claim 5, wherein the driving mechanism is a spur gear system having a drive gear and at least two driven gears.

7. The peripheral peg drill component of claim 6, wherein the at least two driven gears are each independently associated with and configured to simultaneously rotate in the same direction as one of the at least two drill bits.

8. The peripheral peg drill component of claim 5, wherein the driving mechanism is a spur gear system having a drive gear, at least two driven gears and at least two idler gears, each idler gear of which is positioned between the drive gear and one of the at least two driven gears.

9. The peripheral peg drill component of claim 8, wherein the at least two driven gears are each independently associated with and configured to simultaneously rotate in the same direction as one of the at least two drill bits.

10. The peripheral peg drill component of claim 5, wherein the movable boss further comprises a compression spring that is configured to assist with moving the boss from a first position within the housing to a second position outside of the housing.

11. The peripheral peg drill component of claim 10, wherein the movable boss is configured to unitarily collapse the at least two drill bits into the housing as the bony surface is engaged.

\* \* \* \* \*